United States Patent [19]
Quedens et al.

[11] Patent Number: 5,199,432
[45] Date of Patent: Apr. 6, 1993

[54] FETAL ELECTRODE PRODUCT FOR USE IN MONITORING FETAL HEART RATE

[75] Inventors: Phillipp J. Quedens, Berlin; Donald R. Boucher, Wallingford; John T. Shipherd, Madison; Michael J. Malis, Trumbull; Joseph A. Izzo, New Haven, all of Conn.

[73] Assignee: American Home Products Corporation, New York, N.Y.

[21] Appl. No.: 605,843

[22] Filed: Oct. 30, 1990

[51] Int. Cl.$^5$ .................... A61B 5/04; A61B 5/0444
[52] U.S. Cl. ..................... 128/642; 439/909
[58] Field of Search .................. 128/639–642, 128/783–785, 786; 439/530, 668, 669, 877, 909

[56] References Cited

U.S. PATENT DOCUMENTS

| | | |
|---|---|---|
| Re. 28,990 | 10/1976 | Hon et al. |
| Re. 32,204 | 7/1986 | Halvorsen ............... 128/642 |
| 2,318,207 | 4/1941 | Ellis ............... 128/644 |
| 3,580,242 | 5/1971 | LaCroix ............... 128/642 |
| 3,800,800 | 4/1974 | Garbe et al. ............... 128/788 |
| 3,895,635 | 7/1975 | Justus et al. ............... 606/32 |
| 4,061,408 | 12/1977 | Bast et al. |
| 4,073,287 | 2/1978 | Bradley et al. ............... 128/642 |
| 4,090,760 | 5/1978 | Furey |
| 4,094,571 | 6/1978 | Benjamin |
| 4,121,573 | 10/1978 | Crovella et al. |
| 4,180,080 | 12/1979 | Murphy ............... 128/642 |
| 4,209,020 | 6/1980 | Nielsen |
| 4,253,721 | 3/1981 | Kaufman |
| 4,268,101 | 5/1981 | Stone |
| 4,320,764 | 3/1982 | Hon |
| 4,321,931 | 3/1982 | Hon ............... 128/642 |
| 4,353,372 | 10/1982 | Ayer ............... 128/640 |
| 4,384,757 | 5/1983 | Andrews, Jr. et al. |
| 4,437,467 | 3/1984 | Helfer et al. ............... 128/642 |
| 4,522,211 | 6/1985 | Bare et al. ............... 128/640 |
| 4,600,017 | 7/1986 | Schroeppel |
| 4,632,121 | 12/1986 | Johnson et al. ............... 128/640 |
| 4,671,591 | 6/1987 | Archer |
| 4,722,354 | 2/1988 | Axelgaard et al. |
| 4,848,345 | 7/1989 | Zenkich ............... 128/639 |
| 4,869,255 | 9/1989 | Putz |
| 4,894,023 | 1/1990 | Hall |
| 4,911,657 | 3/1990 | Berlin |
| 5,046,965 | 9/1991 | Neese et al. ............... 128/642 |
| 5,135,006 | 8/1992 | Bellinson ............... 128/642 |

FOREIGN PATENT DOCUMENTS

| | | |
|---|---|---|
| 0377432 | 7/1990 | European Pat. Off. |
| 8603542 | 5/1986 | Fed. Rep. of Germany |
| 8701828 | 4/1987 | Fed. Rep. of Germany |
| 1339029 | 11/1973 | United Kingdom |
| 2057784 | 4/1981 | United Kingdom ............... 439/877 |

OTHER PUBLICATIONS

Corometrics Medical Systems, Inc., Leg Plate for Use with Corometrics Model 115, 116 Fetal Monitors, as offered for sale in Catalog No. 2608DAO, Sep. 1988, 5 pages.

*Primary Examiner*—Lee S. Cohen
*Assistant Examiner*—K. M. Pfaffle
*Attorney, Agent, or Firm*—Darby & Darby

[57] ABSTRACT

A connector attached to an end of a twisted wire pair, whose other end has fetal and maternal electrodes. A driving tube is removed from the twisted wire pair by pulling a drive handle and driving tube over the connector. The outer diameter of the connector is smaller than the inner diameter of the driving tube. After the connector is free, it is inserted into a housing of a leg plate, which electrically interconnects terminals of the connector and thereby the electrodes with a remote monitoring device. The housing has finger grips to help hold the housing during the insertion of the connector. The leg plate also has a base which is held in position against a mother's leg and has a ground electrode which is also electrically interconnected with the device. The housing is rotatable relative to the base.

10 Claims, 4 Drawing Sheets

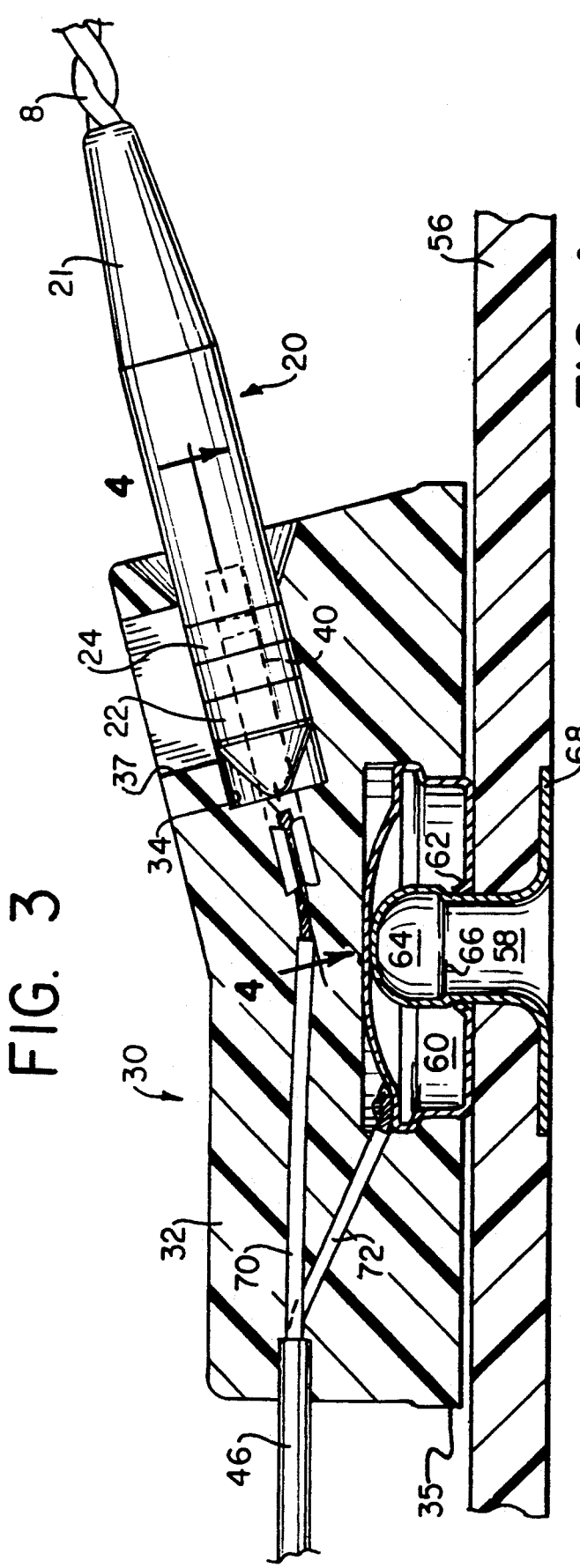

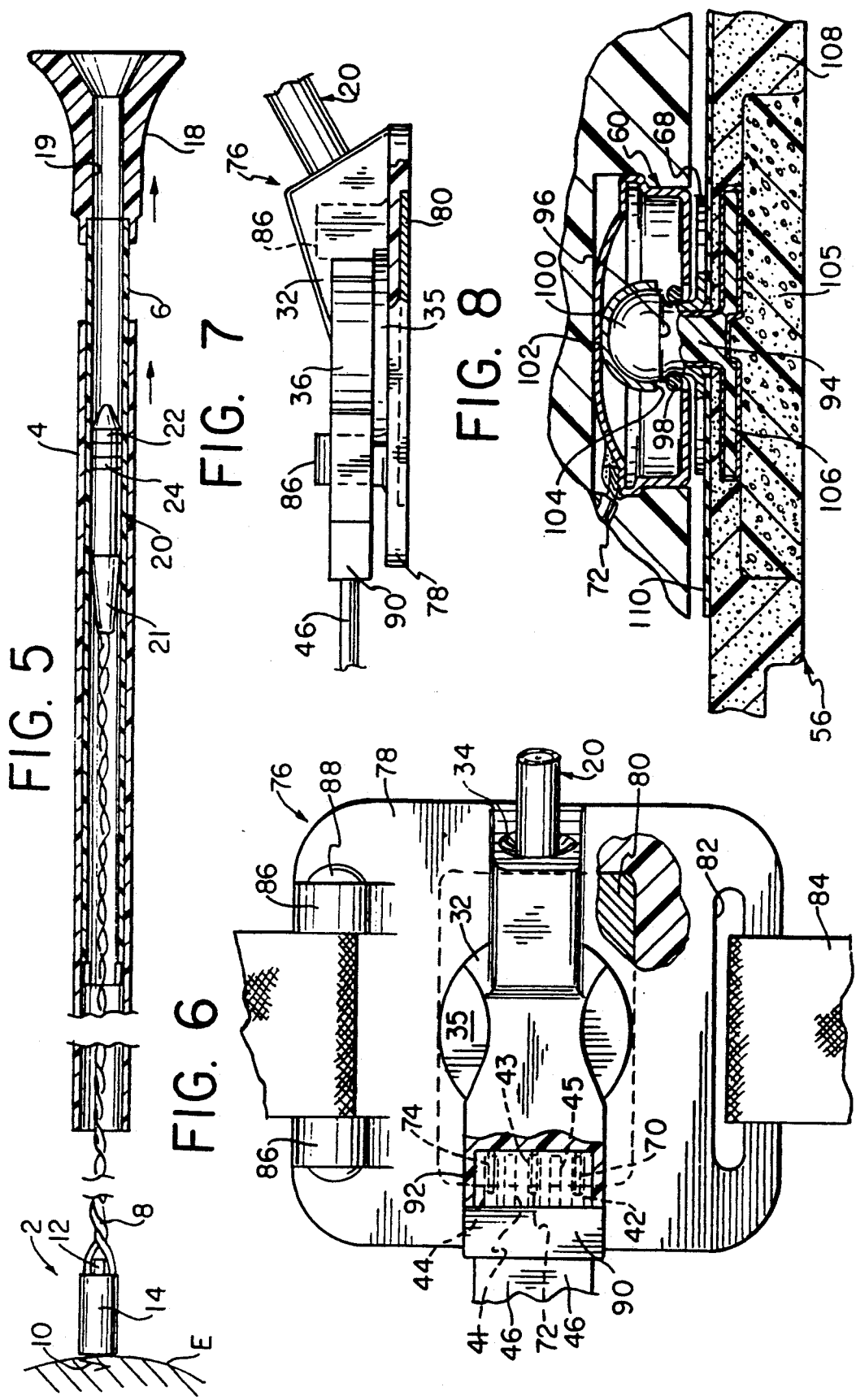

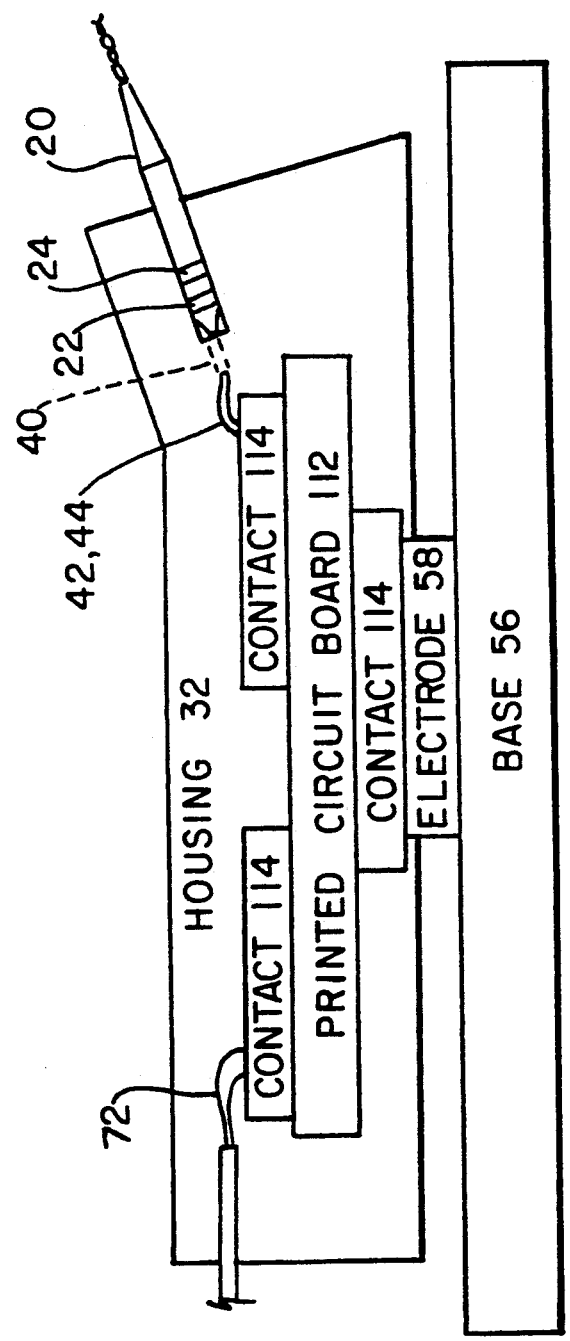

FETAL ELECTRODE PRODUCT FOR USE IN MONITORING FETAL HEART RATE

BACKGROUND OF THE INVENTION

The present invention relates to a fetal electrode product for monitoring fetal heart rate. More particularly, the invention relates to an improved connector device for interconnecting a remote, fetal monitoring device and a bipolar fetal electrode product.

U.S. Pat. No. Re 28,990, which is incorporated herein by reference, discloses the bipolar fetal electrode product commonly used to monitor fetal heart rate during birth. In the use of that product, a doctor inserts the forward end of a curved guide tube through the mother's vagina and cervix until the forward end of the guide tube makes contact with the fetal head or other portion of the fetus. Holding the forward end of the guide tube stationary, the doctor then pushes the rear end of a flexible driving tube forwardly until a spiral fetal electrode at the forward end of one wire of a twisted wire pair makes contact with the fetal epidermis. The forward end of the other wire is connected to a spade-like maternal electrode which is electrically isolated from the spiral fetal electrode.

The doctor then rotates the flexible driving tube clockwise about one full turn while maintaining the forward end of the guide tube against the fetal head. This will screw the spiral electrode into the fetal epidermis. Thereafter, the doctor removes his fingers from the mother's vagina, grasps the outer ends of the driving tube and the guide tube, and slides these tubes as a unit off the wires, leaving only the bipolar electrodes and the two twisted wires within the mother.

The proximal ends of the wires are then connected to a suitable apparatus for monitoring fetal heart rate. Such an apparatus is discussed in U.S. Pat. No. 4,632,121, the contents of which are also incorporated by reference and which shows a cable assembly for effecting electrical connection between the electrodes and the fetal monitor. A galvanic potential difference may then be measured between the bipolar electrodes. The wires connected to the electrodes are twisted about each other so that any induced voltages caused by external electromagnetic interference will be the same in each and therefore will not adversely affect the measurement of the galvanic potential difference between the electrodes.

In practice, the ends of the twisted wires are left uninsulated, e.g. by as much as ⅜ inch to ¾ inch, to allow connection to the monitor and to enable removal of the guide and driving tubes from the twisted wires.

Manually connecting the uninsulated ends of the twisted wire pair to the base plate is somewhat cumbersome and creates the possibility that the wires may unintentionally short each other. If shorted, the wires will be unable to transmit correct signals from the fetal electrodes.

It would therefore be desirable to effect electrical interconnection between the fetal and maternal electrodes and a remote fetal monitoring device without handling uninsulated ends of wires.

SUMMARY OF THE INVENTION

The present invention is directed to an arrangement for establishing electrical connection between fetal and maternal electrodes and a remote fetal monitoring device. The arrangement includes a connector at the proximal end of a twisted wire pair, fetal and maternal electrodes at the distal end of the twisted wire pair, and a removable driving tube which may be pulled over the connector.

It is preferred that the proximal end of the connector be tapered and that an open ended, cone-like driving handle be arranged at the proximal end of the driving tube to facilitate removal of the driving tube by pulling. The driving tube may be pulled from the electrodes together with the guide tube, which surrounds the driving tube.

The connector has electrical contacts which are electrically connected to the proximal ends of the wires of the twisted wire pair. The connector is insertable into an opening of a housing of a leg plate so as to establish contact between the connector contacts and electrical contacts in the leg plate housing.

BRIEF DESCRIPTION OF THE DRAWINGS

For a better understanding of the present invention, reference is made to the following description and accompanying drawings while the scope of the invention will be pointed out in the appended claims.

FIG. 3 is an enlarged cross sectional view taken along the line 3—3 of FIG. 2 showing a leg plate which has a reusable housing detachably connected to a disposable adhesive pad;

FIG. 4 is a cross-sectional view taken along the line 4—4 of FIG. 3;

FIG. 4a is a cross-sectional view taken along the line 4a—4a of FIG. 4.

FIG. 5 is a longitudinal cross-section of the electrode assembly showing the guide and driving tubes being removed from the connected fetal electrode.

FIG. 6 is a top view of a reusable leg plate with provisions for the attachment of monitor and fetal electrode leads.

FIG. 7 is an elevation view of the leg plate of FIG. 6.

FIG. 8 is an enlarged cross-sectional view as if taken along the line 3—3 of FIG. 2, except that for this embodiment, the housing and adhesive pad are fixed to each other.

FIG. 9 shows a diagrammatic schematic of another embodiment.

DESCRIPTION OF THE PREFERRED EMBODIMENT

Figure 1:
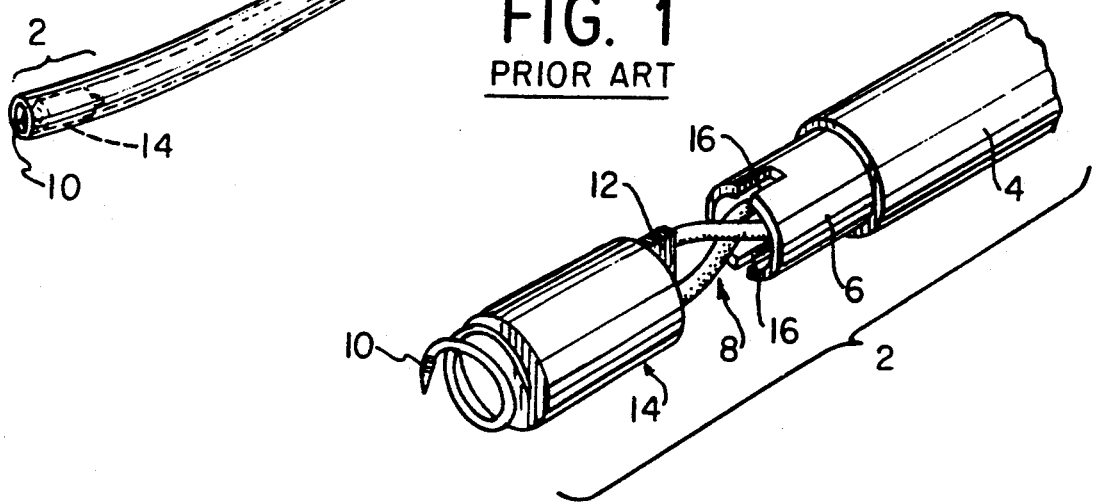
FIG. 1 is a perspective view of the forward end of a bipolar fetal electrode product in accordance with the prior art.

FIG. 1 shows the forward or distal end 2 of a conventional fetal electrode product in accordance with U.S. Pat. No. Re. 28,990. The fetal electrode product includes a guide tube 4, driving tube 6 which is of a smaller diameter than, that of the guide tube 4, and a twisted pair of wires 8 the distal ends of which are connected to respective fetal and maternal electrodes 10, 12. A nonconductive plastic holder 14 electrically insulates the fetal and maternal electrodes 10 and 12 from each other.

The fetal electrode 10 is in the form of a spiral electrode having a pointed end which is driven into contact with the fetal epidermis. The maternal electrode 12 is engageable by slots 16 at the forward end of the driving tube 6 to enable the pointed end of the fetal electrode 10 to rotate and be driven into the fetal epidermis E (see FIG. 5) by rotation of the driving tube 6.

After the spiral electrode 10 has engaged the fetus, the guide and driving tubes 4, 6 may be pulled and removed from the mother, leaving the electrode head and twisted wire pair 8 in the birth canal. In the prior art, the proximal ends (not shown in FIG. 2) of the twisted wire pair were uninsulated bare wire for enabling connection to electrical terminals on a leg plate.

Figure 2:
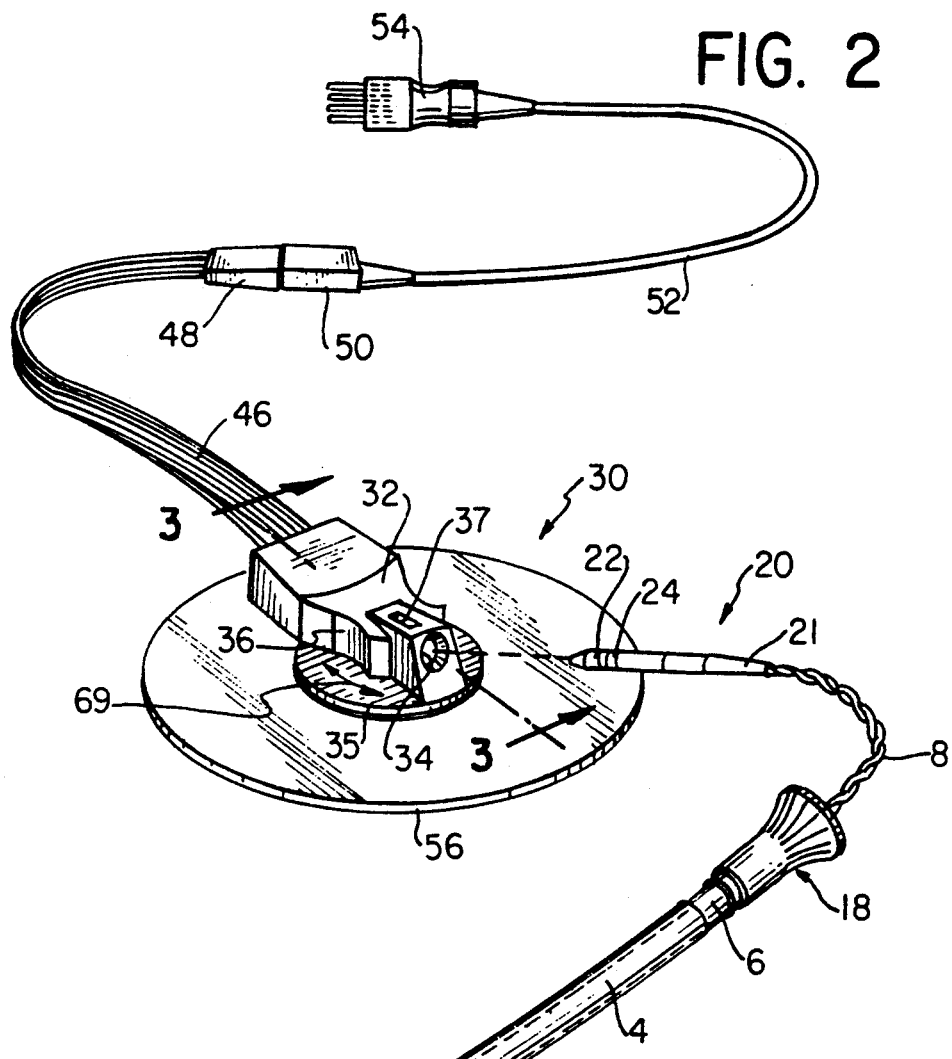
FIG. 2 is a perspective view of the improved connector incorporated in a fetal monitoring system and illustrating a leg plate which may be either disposable or reusable.

FIGS. 2-4 show a connector 20 attached to the proximal ends of the twisted wire pair 8 in accordance with the invention. The connector 20 has electrically conductive ring-shaped contacts or 22, 24 which are connected to uninsulated ends 26, 28, respectively (see FIG. 4) of the twisted wire pair 8. The contacts 22, 24 may extend around the entire circumference of the connector 20 and are axially spaced apart from each other to avoid electrical contact therebetween.

A drive handle 18 defines a passage 19 (see FIG. 5) in communication with the inner passage defined by the driving tube 6. The driving tube 6 is jam fit into handle 18 along an inner taper of handle 18 that extends toward a stepped surface of the handle 18 (see FIG. 5).

Handle 18, which has a cone-like shape facing rearwardly, facilitates pulling of the driving tube 6 off the twisted wire pair 8. The proximal end 21 of the connector 20 is tapered to fit within the tapered proximal end of handle 18 and thereby travel within the driving tube 6 without jamming.

A leg plate 30 (FIG. 2) includes a housing 32 with an opening 34, which is adapted to receive the connector 20 after the driving and guide tubes are removed. Concavely curved finger grips 36 are provided on either side of the housing 32. These grips 36 facilitate holding of the housing while inserting the connector 20 into the opening 34. The bottom of the housing 32 includes an integrally formed circular plate 35.

The outside diameter of the connector body 20 is smaller than the inside diameter of the driving tube 4. Thus, the guide and driving tubes 4, 6 may be pulled together over the connector 20 and thereby removed from twisted wire pair 8 prior to connecting to leg plate 30.

As is seen in FIG. 2, the connector 20 is inserted into the opening 34 in the direction indicated by the dashed lines. As better seen in FIG. 3, the opening 34 defines an elongated path of insertion for the connector 20, which extends about a centerline. As best seen in FIG. 4a, contacts 38, 40 lie radially outside the path with respect to a radial direction from the center line.

As an additional feature, an opening 37 may be provided along the top of the housing 32. This opening 37 provides access for facilitating cleaning of the electrical connections and further allows one to visually verify that electrical connection has been made.

After insertion of the connector 20 into the opening 34 as shown, in FIGS. 3 and 4, spring biased electrical contacts 38, 40 within the housing 32 electrically contact the ring-shaped contacts 22, 24, respectively. The proximal ends of the leg plate contacts 38, 40 form holding clamps which hold uninsulated ends of leads 42, 44, respectively. The leads 42, 44 extend through ribbon cable 46 (see FIG. 2) to a signal receiving socket of a fetal monitoring device via interengaging socket and plug connectors 48, 50, cord 52 and plug 54, which is adapted to be plugged into the fetal monitor. In a similar manner, leads 41, 43, 45 (see FIG. 6), which will be described later, extend through the ribbon cable 46.

FIGS. 2 and 3 also show a base 56 snapped to the underside of the housing 32 via a stud 58 within a snap compartment 60. The base 56 may be an adhesively coated flexible pad made from foam material. In FIG. 3, the stud 58 is pushed between an opening periphery 62 in the underside of the snap compartment until its top rounded end 64 clears the opening periphery 62. In this position the stepped transition area 66 of the stud 58 engages the opening periphery 62. During insertion, the opening periphery 62 bends against the stud 58 into the position shown. The bottom 68 of the stud 58 extends radially outward so as to sandwich the pad 56 between itself and the underside of the snap compartment 60.

The housing 32 is freely rotatable about the stud 58 with respect to the pad 56 in either the clockwise or counterclockwise directions indicated by double arrow 69 (see FIG. 2). This rotation allows the housing 32 to be oriented into any desired angular orientation. This rotatable connection helps to avoid inadvertent disconnection of the removable connector 20 from the leg plate 30 when, for instance, a doctor brushes against the twisted wire pair 8.

FIG. 5 shows the manner of removal of the guide and driving tubes 4, 6 from the connector 20 and twisted wire pair 8. The spiral electrode 10 is in contact with the fetal epidermis E. The tubes 4,6 are removed by pulling the driving handle 18 and guide tube 4 in the direction indicated by the direction arrows, i.e., in a direction away from the fetal and maternal electrodes 10, 12. After removal of the tubes, the connector 20 is inserted into a leg plate.

FIG. 6 shows three leads 42, 43, 44 in electrical connection with leads 70, 72 and 74, respectively (see also FIG. 3). Two other leads 41, 45 (not shown in FIG. 3 for sake of brevity but arranged similar to that shown FIG. 6) are unterminated to serve as shield wires to help shield against stray induced voltages from electromagnetic interference and are electrically connected to a chassis (not shown) of the monitoring device. The unterminated leads 41, 45 act like an antenna to pick up stray voltages in the vicinity and route them to the chassis, rather than allow the stray voltages to follow the path of the other wires. Leads 41, 45 also distribute capacitance from the other three leads 42, 43, 44 via ribbon cable 46 to the chassis.

FIGS. 6 and 7 also show a leg plate 76, which has the same housing 32 as that for the leg plate 30 of FIG. 3, except that the housing is attached to a larger rectangular belt plate 78, rather than to an adhesive pad 56. The belt plate 78 of FIG. 6 has a ground plate 80 welded onto the base 68 (see FIG. 3) of the stud 58.

The belt plate 78 has a slot 82 for holding one end of a belt 84 as shown on one side and holed projections 86 with a pin 88 extending through the holes in projections 86 for holding the other end of the belt 84. The belt plate 78 snaps into the underside of the housing 32 in the same way as does the base 56 so as to enable the housing 32 to rotate about the stud 58. Since the belt 84 is only snugly fit around the mother's thigh and not too tight as to cause restriction of blood flow, the ground plate 80 must be larger than the base 68 of the FIG. 3 embodiment needs to be in order to ensure that contact with mother's leg is maintained.

The belt plate 78 is exemplified by Corometrics Medical Systems as part of leg plate model no. 260800A, C.

A suitable leg plate belt 84 is exemplified by Corometrics Medical Systems as model no. 202300AA.

FIG. 6 also shows a plug 90 from which extends ribbon cable 46 and which is fitted into a socket 92 of the leg plate 76. This differs from the hard wiring of leads 70, 72, 74 from ribbon cable 46 of FIG. 3.

FIG. 8 shows a view similar to that of FIG. 3 except that the stud 94 has an undercut 96 in which is resiliently biased a snap spring 98. Spring 98 is retained in the snap compartment 60 and is ring-shaped to define an opening therethrough.

In order to snap the stud 94 into place, the top rounded end 100 of the stud 94 is inserted through the opening defined by the snap spring 98 and into the compartment 60. A cap 102 is on the top rounded end 100 of the stud 94. During this insertion, the snap spring 98 is forced to elastically expand outward by the cap 102 pressing against the snap spring 98 until the spring 98 clears the downwardly facing end 104 of the cap 102. The snap spring 98 thereafter resiliently closes against the undercut 96 to retain the stud 94 in position. If attempt is made to pull the stud 94 out of the compartment 60, withdrawal of the stud 94 is prevented by the holding force of the spring 98. Thus, a permanent mechanical snapping securement is obtained.

A conductive gel 105 is applied to the base 106 of the stud 94. This gel will contact the thigh of the mother. Although not shown in the other embodiments, the gel 105 is applied to the bases of each of the other embodiments as well. The bases 68, 106 or ground plate 80 serve as ground electrodes.

In both FIGS. 3 and 8 embodiments, the snap compartment 60 is electrically conductive and is in electrical contact with the stud 58 or 94, which is also electrically conductive. Lead 72 has an uninsulated end which is soldered to the snap compartment 60.

In the embodiments of FIGS. 2-4 and 8, the flexible adhesive pad 56 may conform to the shape of the mother's leg when adhered to the leg. A removable sheet (not shown) may cover the adhesive on the underside of the pad 56 and then be removed when the pad 56 is to be applied to the mother's leg. The adhesive pad 56 (see FIG. 8) may include a foam material 108 secured to a sturdier element 110, such as vinyl.

As should be apparent, for any embodiment, the ribbon cable 46 may be either hard wired to the leg plate or may be plugged into a socket in the leg plate. Also, either embodiment may employ either the permanent or detachable snap connection. The advantage of using the detachable snap connection is that the housing may be reused; only the base which is in direct contact with the patient will be discarded. Thus, any base is interchangeable with another.

For all the leg plate embodiments, it is desireable to angle the incline of the opening 34 in the housing 32 for receiving the connector 20 at about eighteen degrees relative to the horizontal plane (or of the adhesive pad 56 or belt plate 78) so that insertion of the connector 20 will not get in the way of the mother's leg. The side of the leg plates which receive the connector may be considered an input and the side which effects connection with the remote monitoring device may be considered an output.

Preferably, the electrodes and electrical contacts and conductors are made of nickel or gold plated copper or else gold plated over nickel plated copper. High density polyethylene (such as 12 melt Arco #7120 or Chevron #9160 or petrothene LS 606 8 melt, density 0.96) is recommended as the material for the guide and driving tubes 4, 6, handle 18 and the housing 32. The conductors are preferably jacketed with polyvinylchloride. All components may be made from the same materials as are described for their counterparts in the patents previously mentioned that are incorporated herein by reference.

The outer diameter of the guide tube 4 must be small enough to avoid harming the mother during its insertion, such as about 0.315 inches. The inner diameter of the driving tube 6 is about 0.146 inches. Thus, the width of the connector 20 must be less than 0.146 inches to fit within the driving tube 6. For example, the maximum diameter of connector 20 may be 0.125 inches.

FIG. 9 shows a further embodiment of the leg plate which utilizes a printed circuit board 112, that is fitted in the bottom of the housing. All interconnection leads are then soldered directly to contacts 114 on the printed circuit board below. The board is preformed so that all leads will be in alignment with respective contacts after placing the board in the housing. The printed circuit board may interconnect the appropriate contacts.

If desired, the housing may be prevented from rotating relative to the base by providing projections from the base which block the housing from rotating.

While the foregoing description and drawings represent the preferred embodiments of the present invention, it will be understood that various changes and modifications may be made without departing from the spirit and scope of the present invention.

What is claimed is:

1. A fetal electrode product for use in monitoring fetal heart rate, said product being used in conjunction with a fetal monitor coupling device supported on the mother's body and having a housing with an opening, said product comprising:
    a fetal electrode, a maternal electrode and a holder made of an insulating material, said electrodes secured to said holder;
    a connector dimensioned and shaped to be received in the opening in the coupling device housing and having at least two contacts separated and electrically isolated from each other, said contacts positioned to make electrical contact with complementary contact members in said coupling device;
    an insulated pair of elongated flexible wires, each of said wires electrically connecting a respective one of said contacts to a respective one of said fetal and maternal electrodes; and
    an elongated, flexible driving tube for rotating said holder, said driving tube defining a tubular channel in which the wires extend, the tube being displaceable relative to the wires in a direction away from the electrodes, the connector having an outer dimension which is less than the inner diameter of the driving tube so as to allow the connector to pass through the driving tube as the driving tube is pulled in the direction away from the electrodes to thereby cause the wires to leave the tubular channel.

2. A fetal electrode product according to claim 1, wherein said connector is elongated and made of an insulating material, at least a proximal portion of said connector being cylindrical, said contacts comprising axially spaced apart electrically conductive rings on said cylindrical proximal portion of said connector, said wires extending within said connector and being electrically connected to respective ones of said conductive rings.

3. A fetal electrode product according to claim 2, wherein said connector includes a distal portion extending from said cylindrical proximal portion of said connector on which said conductive rings are mounted.

4. A fetal electrode product according to claim 3, wherein said distal portion of aid connector is tapered from a larger diameter to a smaller diameter section in a direction away from said conductive rings.

5. A fetal electrode product according to claim 4, wherein said connector includes means cooperating with said coupling device for positioning said connector in a predetermined location within said coupling device.

6. A fetal electrode product according to claim 4, wherein a handle is secured to a proximal end of said driving tube, said handle including a tapered opening in its proximal end to facilitate removal of said driving tube over said connector.

7. A fetal electrode product according to claim 1, wherein said connector is elongated and made of an insulating material, said contacts comprising axially spaced apart, electrically conductive rings, said wires extending within said connector and being electrically connected to respective ones of said conductive rings within said connector.

8. A fetal electrode product according to claim 7, wherein said connector includes a distal portion tapered from a large diameter section to a small diameter section in a direction away from said conductive rings.

9. A fetal electrode product according to claim 8, wherein said connector includes means cooperating with said coupling device for positioning said connector in a predetermined location within said coupling device.

10. A fetal electrode product according to claim 8, wherein a handle is secured to a proximal end of said driving tube, said handle including a tapered opening in its proximal end to facilitate removal of said driving tube over said connector.

* * * * *